(12) United States Patent
Seth

(10) Patent No.: US 12,308,106 B2
(45) Date of Patent: May 20, 2025

(54) MINDSET MASTERY: NEXT-GEN HEALING WITH AI-DRIVEN VR VISUALIZATION

(71) Applicant: Pankhudi Seth, Toronto (CA)

(72) Inventor: Pankhudi Seth, Toronto (CA)

( * ) Notice: Subject to any disclaimer, the term of this patent is extended or adjusted under 35 U.S.C. 154(b) by 0 days.

(21) Appl. No.: 18/444,260

(22) Filed: Feb. 16, 2024

(65) Prior Publication Data

US 2024/0282428 A1     Aug. 22, 2024

Related U.S. Application Data (60) Provisional application No. 63/446,243, filed on Feb. 16, 2023.

(51) Int. Cl.
*G16H 20/70*        (2018.01)

(52) U.S. Cl.
CPC .................................. *G16H 20/70* (2018.01)

(58) Field of Classification Search
None
See application file for complete search history.

(56) References Cited

U.S. PATENT DOCUMENTS

| | | | |
|---|---|---|---|
| 6,643,385 B1 | 11/2003 | Bravomalo | |
| 6,896,655 B2 | 5/2005 | Patton et al. | |
| 8,205,367 B2 | 6/2012 | Markos | |
| 8,517,912 B2 | 8/2013 | Clare | |
| 9,069,648 B2 | 6/2015 | Jones | |
| 9,501,942 B2 | 11/2016 | Kaleal et al. | |
| 2012/0254749 A1* | 10/2012 | Downs, III | G16H 40/67 715/706 |
| 2014/0075337 A1 | 3/2014 | Hunter | |
| 2016/0005320 A1 | 1/2016 | deCharms et al. | |
| 2016/0171180 A1* | 6/2016 | Yagnyamurthy | G16H 20/70 705/3 |
| 2017/0353711 A1 | 12/2017 | Wayenberg | |
| 2019/0080794 A1* | 3/2019 | Moskowitz | G16H 20/70 |
| 2020/0279498 A1 | 9/2020 | Ribeira et al. | |
| 2021/0043011 A1 | 2/2021 | Gates | |
| 2021/0186339 A1* | 6/2021 | Pfister | G10L 21/007 |

(Continued)

FOREIGN PATENT DOCUMENTS

| | | |
|---|---|---|
| WO | 2007016241 A2 | 2/2007 |

*Primary Examiner* — Nicholas J Lee (74) *Attorney, Agent, or Firm* — Bold IP PLLC; Christopher Mayle (57) ABSTRACT

A system and method designed to revolutionize disease treatment by harnessing the power of virtual reality to simulate potent neuroimmunology waves, effectively targeting illnesses and disabilities. Powered by an AI system incorporating deepfake technology coupled with VR, our solution maximizes the effectiveness of visualization towards healing. Moreover our solution dynamically refines over time, integrating feedback from diverse health monitoring devices, user input, and past outcomes. Beyond medical applications, our approach extends to empowering individuals through visualization, enabling them to envision achieving goals and overcoming obstacles. Furthermore, our platform provides vital mental health support, offering personalized visual narratives to combat depression and related challenges. With collaboration from esteemed professionals and ongoing refinement, the invention aims to catalyze positive change on a global scale, enhancing mental well-being for all.

16 Claims, 7 Drawing Sheets

Visualization System 100

(56) References Cited

U.S. PATENT DOCUMENTS

| | | |
|---|---|---|
| 2021/0375153 A1 | 12/2021 | Kalhil |
| 2022/0008745 A1* | 1/2022 | Kirchner ................ G16H 50/20 |
| 2022/0051582 A1 | 2/2022 | Sy |
| 2023/0104450 A1* | 4/2023 | Garriga Calleja ..... G16H 50/20 705/2 |
| 2023/0126476 A1* | 4/2023 | Han ....................... G16H 20/70 705/2 |

* cited by examiner

MINDSET MASTERY: NEXT-GEN HEALING WITH AI-DRIVEN VR VISUALIZATION

CROSS REFERENCE TO RELATED APPLICATIONS

This application claims priority to U.S. Provisional Patent No. 63/446,243 filed on Feb. 16, 2023, which is incorporated in its entirety.

FIELD OF THE DISCLOSURE

The overall invention is a visualization system that enables users to visualize themselves in various scenarios, such as achieving or experiencing their desired goals or overcoming challenges through videos and images that are personalized by the application of deepfake systems and AI algorithms that improve over time using user feedback, various health monitoring parameters, and previous results. Additionally, it generates goal-specific affirmations and stories generated by a specialized machine learning model, available in both text and audio formats.

BACKGROUND

In today's fast-paced digital age, the significance of personalized experiences, especially in the realm of self-help and medical support, has become paramount. Envisaging a solution that bridges personal aspirations with technology, the inventor has conceptualized a system that combines deep fake technology, artificial intelligence, and various health monitoring parameters. This app aims to assist and uplift individuals facing challenges ranging from medical conditions and personal goals to athletic pursuits.

There are multiple motivations that are presented in the creation of this invention. The first motivation is directed to the need for a visual system for medical applications. Individuals facing terminal illnesses or mental health issues may adopt a mindset that prevents them from thinking positively or envisioning themselves overcoming their condition. This negative mindset increases the likelihood of giving up easily. Research indicates that one's mindset plays a significant role in determining the speed of their recovery process.

According to a study, it is a proven fact that a patient's mindset is the principal component that determines the pace of a person's recovery or how their body responds to a given treatment. According to other research, a majority of the patients suffering from mental illnesses and terminal diseases have the following mindset: limited ability to see possibilities and opportunities, seeing challenges and setbacks as insurmountable obstacles, and prone to give up easily or feel like a victim of their circumstances. It is evident from the above and much research around the globe of the profound effect of unhealthy mindsets on not only physical health but mental and emotional well-being as well. This also is very important in the world of sports and athletics where players may have trouble coming back from injury based on mindset and may become reinjured.

The system proposed is directed to altering the mindset of a patient by regularly inducing positive vibes using the popular method of visualization. This visualization does not show random positive photos/videos but instead is a personalized experience for the patient where they will view themselves having overcome their specific disease/condition/disability and leading a normal and happy life. To further enhance the experience, this video is rendered through a VR box (or 3-D glasses/any other advanced video rendering technology) which ensures an immersive experience for the patient.

The human brain is designed to focus either on pain or pleasure at a time. This time of exposure to our system will ensure the experience of pleasure and relaxation for patients for a fixed time period every day is aimed at producing positive/desirable neurological responses on every application and improving their vitals/medical parameters instantly or over time.

The second motivation is directed to the need of a visualization system to train the mind to achieve our personal goals or overcome shortcomings. Every person today is striving to achieve a certain goal in their lives. While working hard towards your goal is important, thinking positively throughout the path to achievement is equally important. Today, the technique widely called the "Law of Attraction" is commonly used throughout the world as a powerful tool for manifesting your life goals. People use many techniques to effectively apply the law of attraction in their lives, like using Vision boards on their walls and applying visualization techniques.

Visualization is mentally picturing what you want. Seeing the goal as already complete in your mind's eye is a core technique used by the world's most successful people. Visualization is effective because it harnesses the power of our subconscious mind. The basic idea behind visualization is that in order to get what you want in life; you have to be able to picture that you already are in the position of whatever it is that you want.

However, imagining yourself above all your sufferings is usually challenging for many people, which keeps many from practicing visualization effectively. Moreover, effective visualization comes with patience, focus, and regular practice hence many people are often frustrated before they get the hang of it and realize its fruits. Thus exists a need for a new system and method for visualization which is much more applicable in today's busy world with unfocused minds.

These motivations may be brought into reality with "deepfake" technology. Deepfake is a term that first emerged in 2017 to describe realistic photo, audio, video, and other forgeries generated with artificial intelligence (AI) technologies and is becoming more mainstream. As exciting and promising as deepfake technology is, there are very real threats to it such as significant risks to individuals, institutions, and society by enabling the creation of highly convincing fake videos or audio recordings that can be used for malicious purposes, such as spreading misinformation, defamation etc. However, with this technology, many benefits may be found in the right hands. For instance, using our proposed system we can empower patients to cultivate resilience and a positive outlook, thereby enhancing their prospects for healing and well-being. This is particularly effective for treating individuals grappling with terminal illnesses or mental health challenges that often encounter a debilitating mindset that hinders their ability to even envision recovery and thus leading to premature surrender.

SUMMARY

Our revolutionary application merges deepfake technology, artificial intelligence, and user feedback with health monitoring devices to offer personalized solutions for overcoming diverse challenges. From medical conditions to personal aspirations, athletic endeavors, and even terminal illnesses, our system employs advanced video rendering technology (like VR) to simulate potent neuroimmunology waves, adapting dynamically through user feedback. It extends beyond healthcare, serving as a visualization tool, allowing users to envision their goals with unprecedented realism and versatility, potentially transforming lives across various domains.

The system crafts personalized short videos or images portraying users overcoming various obstacles, including medical challenges for healthcare applications or achieving personal goals or overcoming shortcomings for broader use. Leveraging deepfake technology, users can vividly visualize themselves realizing their aspirations. These visuals, enhanced by an AI recommendation engine, evolve over time through feedback from a Health Data Processing system, incorporating diverse health metrics, or direct user input. Additionally, to enhance immersion, the content may be experienced through virtual reality.

Initially, this system uses patient information (basic information on the patient and their condition which may be entered by the attending nurse as inputs to the system) to curate the videos from a video library that may be created, or collected from various sources using machine learning related algorithms and could be stored on cloud or any future storage technologies or even created dynamically.

The user could be selected from predefined goals or may even enter their goals into a text entry whereby the system has been trained on a vast array of data on the internet for understanding context, and generating goals that are coherent and relevant to the input it receives.

The system utilizes a search algorithm to process queries, searching a video database that may be internally maintained or accessed via APIs from platforms like YouTube or Vimeo. Retrieved videos, each accompanied with a title, description, are then passed to the deepfake system to replace actors' entities with the target user. Users can provide feedback on video relevance, aiding in algorithm refinement and training.

The system enables both manual and dynamic video creation utilizing a tailored ML algorithm capable of leveraging various neural network architectures, such as RNNs, LSTM, CNN, BERT, and others. These videos may feature audio with positive affirmations or stories for an enhanced user experience. The ML modules encompass diverse algorithms, including existing ones, new developments, or hybrids, trained on datasets from public, private, or any internet sources.

Subsequently, user images are utilized as inputs to generate deepfake videos based on ML-curated content delivered to the user. Continuous monitoring of brain waves or relevant medical parameters during the experience feeds into a specialized recommendation engine which does reinforcement learning by continuously improving video curation for individual users and those with similar goals or health conditions. This holistic system may be called the Adaptive Content Curator Engine.

Within our comprehensive framework, the Adaptive Content Curator Engine serves as a specialized recommendation engine, leveraging data processed by the Health Data Processing system as well as user's feedback. This artificial intelligence system crafts personalized and uplifting narratives tailored to patients' specific health conditions, drawing insights from individual health monitoring parameters. Continuously refining its understanding and decision-making abilities, the Adaptive Content Curator Engine analyzes feedback derived from diverse health metrics to enhance its content and recommendations over time.

Employing advanced algorithms, this system learns patterns, identifies correlations, and dynamically adjusts its recommendations and interventions, aiming to optimize and personalize curated content for individuals.

BRIEF DESCRIPTION OF THE DRAWINGS

Embodiments of the present disclosure are described in detail below with reference to the following drawings. These and other features, aspects, and advantages of the present disclosure will become better understood with regard to the following description, appended claims, and accompanying drawings. The drawings described herein are for illustrative purposes only of selected embodiments and not all possible implementations and are not intended to limit the scope of the present disclosure.

DETAILED DESCRIPTION

The present invention is directed to a visualization system that is used for various purposes. The visualization system has a recommendation engine that curates a video of the user fulfilling their goal or overcoming health related problems such as diseases. In both the goal orientated video and the medical related video, the user uploads their photographs which are used as inputs for deepfake technology. The created video may then be displayed to the user through the application or a web interface. When used for medical related purposes, the user may be connected to certain health monitoring related devices that send the feedback to the curation engine for monitoring and as feedback to the Adaptive Content Curator Engine while in use.

The present invention provides personalized visualization videos whereby through deep fake technology, users will be able to see themselves in a variety of life scenarios, which has the potential to bolster confidence and optimism. This feature embodies the phrase, "seeing is believing," allowing individuals to witness themselves overcoming obstacles or achieving dreams. The present invention provides customized storylines whereby a library of adaptable stories that cater to each individual's unique life situations or aspirations ensures a deeply personalized user experience. The present invention provides personalized profiles that will facilitate the delivery of content that remains relevant and tailored to each user's needs and goals The present invention provides diverse catering to a wide spectrum of conditions, goals, and diseases; these templates serve as a foundation on which the personalized stories are built. The present invention provides diverse text to speech with an immersive auditory experience that complements the visual, enabling users to connect more profoundly with the storylines. The present invention provides diverse feedback from a Health Data Processing system, incorporating diverse health metrics while integrating advanced sensors to monitor user reactions. This feature aims to fine-tune the app's content recommendations and ensure the visualization remains as impactful as intended. The present invention provides goal based personalized affirmations designed to reinforce motivation, positivity, and mental strength.

Figure 1:
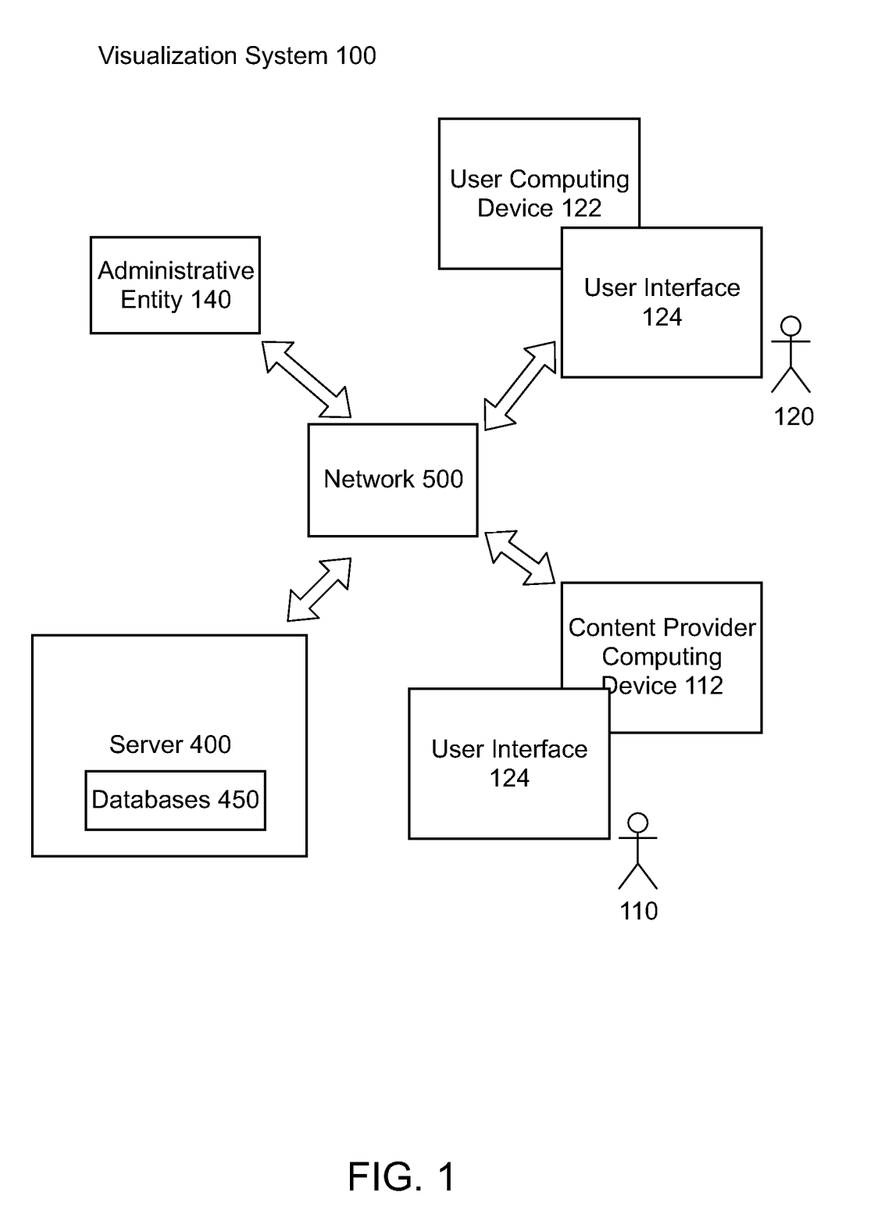
FIG. 1 illustrates the components of the visualization system.

FIG. 1 is a block diagram constructed in accordance with the principles of the current invention. Visualization system 100 may include one or more content such as images or videos that may be stored, collected, extracted, or acquired from a number of content providers such as content providers 110 operating on a content provider computing device such as content provider computing device 112 wherein content is collected by Visualization system 100 after being sent to a database or API such as database 450 for training purposes and future visualization of goals. Visualization system 100 may be extended/adapted to be used for any medical condition which involves experiences of pain. Visualization system 100 may be implemented into a hospital system or other database for patients trying to overcome various problems and ailments.

In some embodiments, visualization system 100 may be innate, built into, or otherwise integrated into existing platforms such as iOS, Android, or social media platforms like Snapchat, TikTok, Instagram or other generational equivalents etc. Content provider computing device 112 may acquire various forms of content from input devices installed or connected to content provider computing device 112 such as microphones, speakers, and applications that may be configured to generate content to be uploaded to Visualization system 100.

In other embodiments, visualization system 100 may be integrated with any latest visualization techniques currently in the market including Augmented reality projections, VR, 3D screens/glasses, 4D screens/glasses, or other technology further evolved in the market (generational equivalents) as deemed suitable for the purpose.

In one or more non-limiting embodiments, content may be directly uploaded to visualization system 100 by a monetization network. Content providers 110 may receive compensation, such as monetary rewards or discounts, for granting access to their content. Users 120 within visualization system 100 are presented with personalized content, incorporating their images and preferences to visualize and pursue their goals.

Databases 450, content providers 110, and users 120 may be distributed across different physical locations. Users 120 interact with visualization system 100 through a user interface like user interface 124, accessible via computing devices such as user computing device 122. User interface 124 features selectable buttons or icons, allowing users 120 to direct visualization system 100 to execute specific processes in response to their selections.

Databases 450, content provider computing devices 112, and user computing device 122 may communicate with one or more servers 400, such as server 400, via networks like network 500. Server 400 could be situated at a data center or other suitable location for network 500 service provision, either centrally or in various distributed arrangements. Server 400 may function as a database server, supporting various database types like centralized, distributed, cloud, NoSQL, relational, network, hierarchical, object-oriented or other futuristic databases. It may utilize storage systems for software applications and data, receiving and coordinating request fulfillment alongside other servers. Server 400's computing systems could resemble those of content provider computing device 112 and user computing device 122.

The servers can be located remotely, interconnected through computer networks or cloud-based networks like the Internet, or locally on electronic devices such as computers or mobile phones. They may take the form of virtual computers, dedicated physical devices, shared physical computers, or computer service daemons. Utilizing cloud serverless infrastructure, comprising hardware and software elements for cloud computing and serverless architecture, enables scalable computing power, networking, storage, and user access interfaces. This infrastructure, including features like virtual private clouds for resource isolation and auto-scaling based on demand, facilitates efficient deployment of processes with minimal operational overhead.

In various embodiments, network 500 encompasses diverse networking environments, including local area networks (LANs) like company Intranets, metropolitan area networks (MANs), or wide area networks (WANs) such as the Internet or World Wide Web. It may comprise private, public, or hybrid networks, spanning telecommunications, wireless (e.g., Wi-Fi), and wireline networks, including mobile telephone networks utilizing protocols like GSM, GPRS, CDMA or any protocols relevant in the future etc. Different data types may be transmitted through network 500 using various protocols, while content provider computing devices 112 and user computing devices 122 may function independently or as peer machines within a peer-to-peer or distributed network setup.

Network 500 may incorporate terminals, gateways, and routers, employing various cellular access technologies such as 2nd (2G), 3rd (3G), 4th (4G), 5th (5G), LTE, GSM, GPRS, EDGE, and others. These technologies enhance coverage between computing devices, particularly in remote locations inaccessible by other networks.

Visualization system 100 may feature administrative entity 140, which, although depicted as a single entity communicating via network 500, may be distributed across multiple physical locations in various embodiments. Administrative entity 140 can manipulate software and input commands to server 400 using input devices like keyboards and mice, with output displayed on a screen.

Server 400 may comprise multiple modules, executed on computing devices akin to user computing device 122 and content provider computing device 112. These modules, such as content processing, data collection, notification, and data aggregation, facilitate diverse functions within visualization system 100. They could be written in languages like C, C++, Java, Python and other future programming languages; these software instructions interact with server 400's operating system to process data stored in databases like databases 450.

Modules may be configured to receive commands or requests from user computing device 122, server 400, content provider computing device 112, databases 450, and external devices via network 500. Server 400 encompasses components, subsystems, and modules supporting management services for visualization system 100. For example, the content processing module may analyze relevant content from content provider 110, leveraging data-mining capabilities based on previously collected data.

Figure 2:
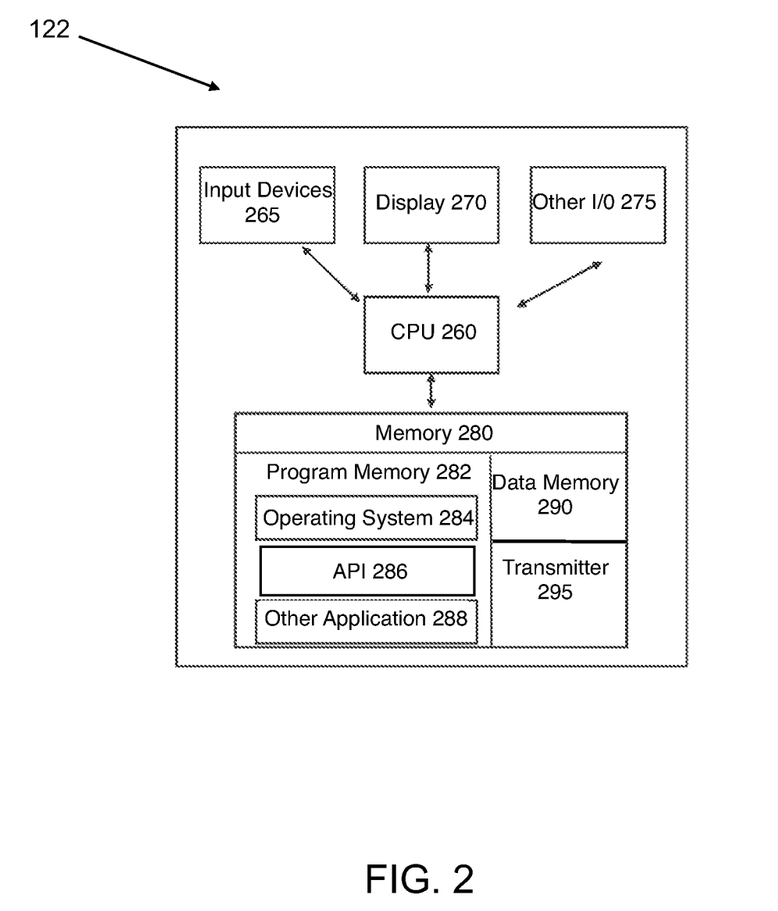
FIG. 2 illustrates the components of the computing device.
Figure 3:
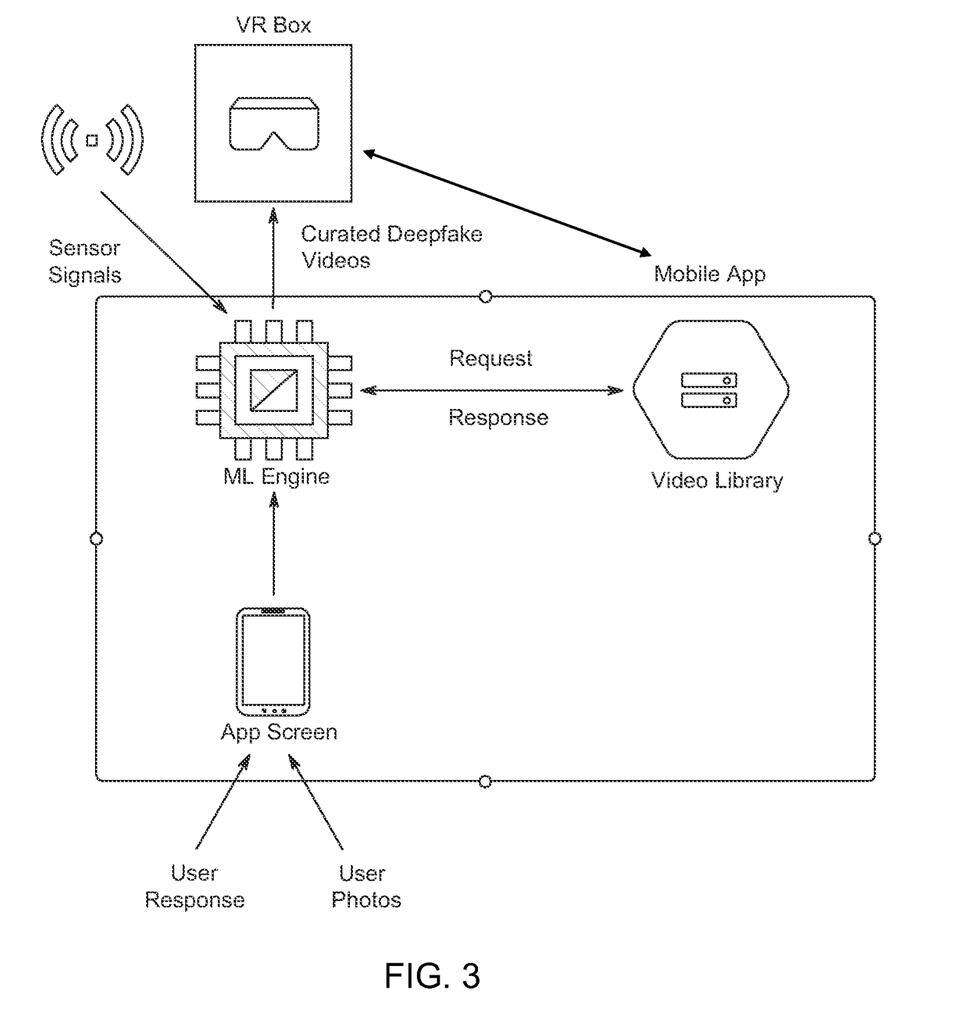
FIG. 3 illustrates the black box representation of the system

One or more embodiments of user computing device 122 and content provider computing device 112 are elaborated in FIG. 2. Equipped with hardware components, they facilitate access to edit and query visualization system 100. These devices feature input devices like input devices 265, notifying CPU 260 of actions through a hardware controller interpreting signals and communicating them to the CPU via a communication protocol. Input devices 265 encompass options like mouse, keyboard, touchscreen, infrared sensor, touchpad, wearable input device, camera- or image-based input device, microphone, and others.

CPU 260, whether single or multiple processing units distributed across devices, communicates with other hardware components like memory devices via buses such as PCI or SCSI. Display 270, utilized for textual and graphical output, provides visual feedback to users. It may include input capabilities, especially if it's a touchscreen or integrates an eye direction monitoring system. Display options range from LCD and LED screens to hologram projectors, virtual reality displays, augmented reality devices, wearable electronic glasses, and more.

Additionally, I/O devices like I/O devices 275 may connect to the processor, incorporating network cards, video cards, audio cards, USB or cameras, printers, and speakers. CPU 260 accesses memory 280, comprising various hardware devices for volatile and non-volatile storage, encompassing RAM, CPU registers, ROM, and writable non-volatile memory like flash memory. Program memory 282 within memory 280 stores software such as operating systems, APIs like API 286, and application programs. Data memory 290 may include database query results, configuration data, settings, user preferences, etc., available to program memory 282 or any component of user computing device 122 and content provider computing device 112.

Memory 280 may include program memory such as program memory 282 capable of storing programs and software, such as an operating system such as operating system 284, API such as API 286, and other computerized programs or application programs such as application programs 288. Memory 280 may also include data memory such as data memory 290 that may include database query results, configuration data, settings, user options or preferences, etc., which may be provided to program memory 282 or any element of user computing device 122 and content provider computing device 112.

Display 270 encompasses various content rendering devices, including binocular head-mounted displays (HMDs), head-mounted goggles (HMGs), augmented reality devices, virtual reality glasses, scope and monocular simulators, hologram projectors, binoculars and telescope simulators, as well as technologies like Google Glass™, connecting to computing devices for users to view virtual environments. Visualization system 100 utilizes cutting-edge video and audio rendering technologies alongside or in lieu of virtual reality to achieve its objectives.

In one or more non-limiting embodiments, display 270 may extend to mobile devices or other platforms. For instance, a mobile device camera can capture surrounding video, enabling users to interact with augmented reality by adding annotations, comments, virtual objects, pictures, audio, and video within the device's range. These virtual objects, including characters and static elements, are rendered by the augmented reality networking system integrated into the system.

User computing device 122 integrates multiple detectors mounted on its housing or connected components. These detectors, ranging from infrared (IR) to radio frequencies, magnetic fields, and ultrasonic sensors, detect people, devices, or environmental cues. Optical sensors capture fingerprint images, while other sensors identify vein patterns and provide real-time biometric measurements like heart rate, heart rate variability, brain waves, blood flow, blood pressure, and more. High dynamic range infrared (IR) sensors enhance detailed image capture of biometric samples.

The system may standardize biometric data into an index value and analyze it in near real-time to determine if it falls within a predefined threshold range. If the index value deviates from this threshold, the adaptive content curator engine may dynamically adjust the video content or incorporate it into future training models for improved customization.

User computing device 122 and content provider computing device 112, may potentially be mobile devices like iPhones, Android or Windows phones, but aren't limited to these and can be any computing device capable of executing instructions with sufficient processing power and memory, including tablets, televisions, desktops, laptops, wearables, routers, or switches. These devices may feature location tracking via technologies like Mobile Location Determination System (MLDS) or Global Positioning System (GPS), leveraging satellite radios for geolocation.

Users 120 may register with visualization system 100 through Visualization API 286, either by downloading/installing the system on their devices or accessing it via a web browser through an extension or plugin. During registration, users may provide basic information like email, username, password, phone number, and address. They may authorize access to external data sources such as patient databases or social networks, allowing the system to collect relevant information for customization.

Upon successful authentication, users are presented with personalized user pages, subject to modification or deletion by both users and administrative entity 140. These pages, accessible through user interfaces like tabs or navigational buttons, offer various subpages catering to user preferences and actions.

Figure 4:
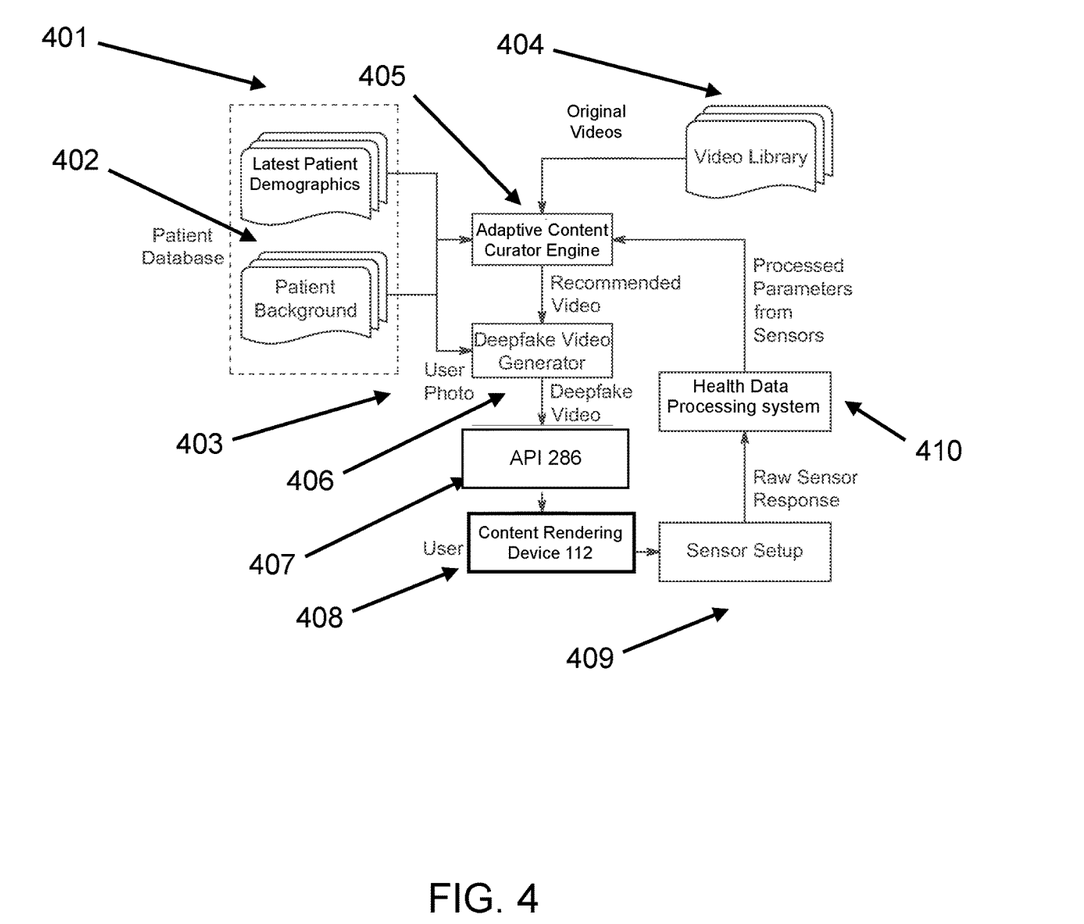
FIG. 4 illustrates the Internal flow of the ML engine for the Medical application
Figure 5:
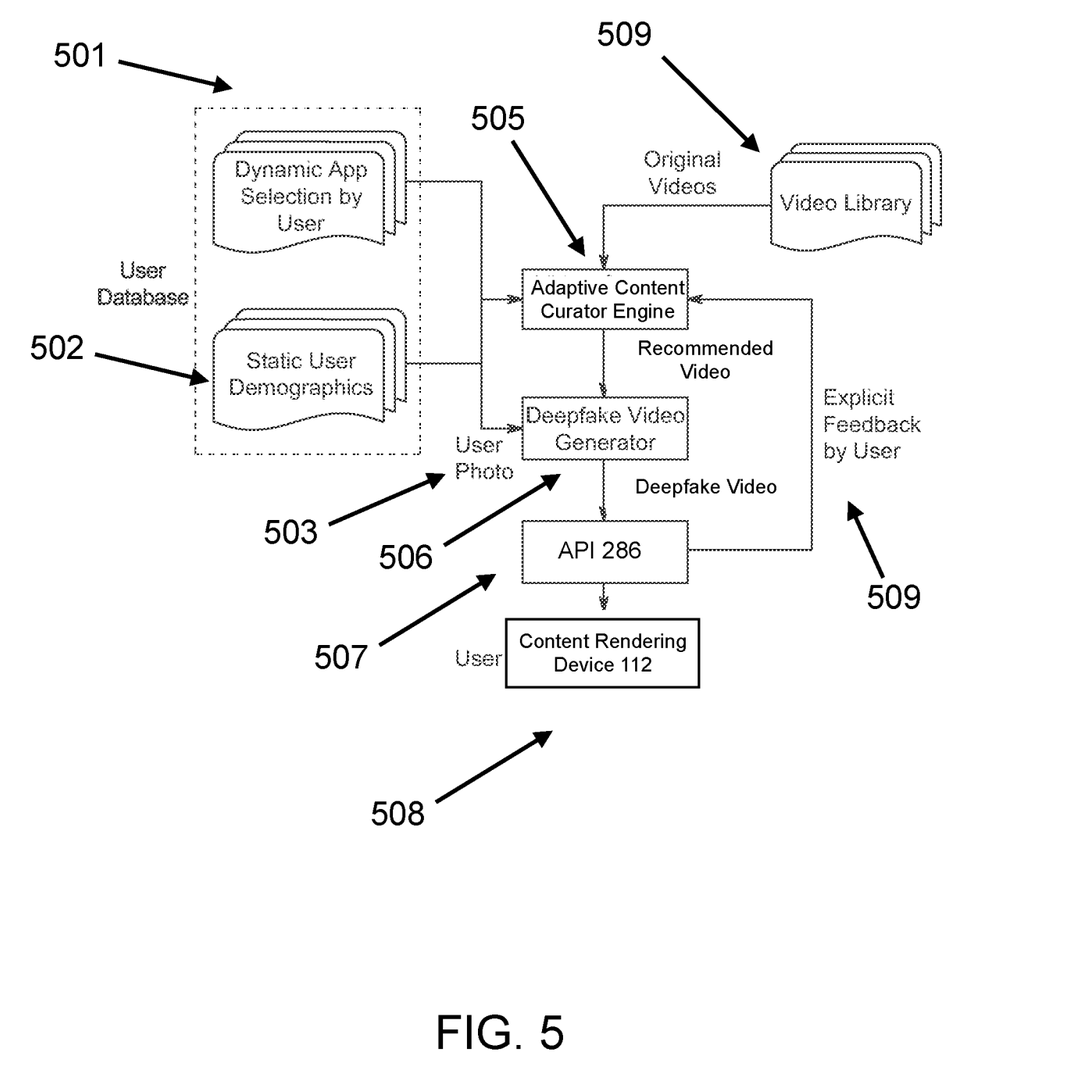
FIG. 5 illustrates the Internal flow of the ML engine for the Goal-based application

User 120 may authorize visualization system 100 to access information or other data from external sources operated by user 120 or associated with the user such as patient background and latest patient demographics from a patient database, as illustrated as block 401 and 402 in FIG. 4 or dynamic application selection by user 120 or static user demographics as illustrated as block 501 and 502 in FIG. 5. In one or more non-limiting embodiments, user 120 may be required to provide credentials to a third-party service provider to allow access by visualization system 100.

User 120 may also authorize social network access whereby when a social network service is linked to visualization system 100, access may be granted to various accounts of user 120 and importing of data from those accounts may occur such as to import one or more social network images or videos. If user 120 authorizes access, the data collection module collects or otherwise accesses certain information and stores the information in databases 450.

Upon successful authentication of user 120, a user page may be generated. The user page may be modified, deleted, written to, or otherwise administered by their respective user 120. Administrative entity 140 may modify or delete a user profile page, for example, as a result of inactivity or inappropriate action. Display to user 120 through user interface 124 may comprise a number of different subpages viewable or accessible through user interface 124 by selecting one or more tabs or navigational buttons.

Upon completion of the user profile, Visualization system 100 generates introductory descriptions outlining the application's functionalities, usage guidelines and privacy policies etc for new users, which may be omitted for returning users. Once users acknowledge these instructions, the system creates a visualization graphical user interface to facilitate the curation of goal-oriented or ailment-overcoming content. This interface allows users to input information, such as photos or keywords, and associate them with mindset goals selected from a predefined list or entered manually, including examples like "Happiness," "Overcoming cancer," "Marriage," "Promotion," "Vacation at a specific destination," or "Leadership."

The visualization user interface offers questionnaires to users 120, aimed at understanding their goals and aspirations. These questionnaires gather crucial information to provide tailored guidance based on users' needs. Presented electronically on user interface 124, the questionnaires feature ratings or multiple-choice questions, with users responding directly through the interface. Responses are then transmitted and stored in database 450, associated with user profile information, ensuring personalized assistance. In some instances, questionnaires may be administered via mail, email, or telephone to cater to user preferences.

The questionnaire responses are stored in databases 450, alongside previous answers, providing a comprehensive history of user 120's interactions with visualization system 100. This continuous feedback loop allows for personalized support as users progress towards their goals. Additionally, users 120 can upload content, such as videos or images, via user interface 124, which is collected and stored by the data collection module in databases 450 for later integration into curated videos using deepfake technology (as depicted in blocks 403 and 503 in FIG. 4 and FIG. 5).

Upon selecting content to upload, users 120 are prompted to associate it with specific goals or ailments, with options drawn from previous user input or customized labels. Visualization system 100 then categorizes and saves the content accordingly. Users may also input goals via text entry, leveraging the system's training on diverse textual data to generate relevant and coherent goals based on user input.

The system employs various deep learning models, such as encoder-decoder neural networks, to automatically extract hierarchical features from images and textual data. For instance, the encoder converts input text into vectors using embeddings that capture semantic meaning, while positional encodings provide information about word sequence positions.

A Multi-Head Self-Attention Mechanism may then be used to allow the model to weigh the importance of different words in the input sequence differently. Each 'head' in the multi-head attention mechanism performs attention independently, allowing the model to capture different types of relationships between words. After the self-attention mechanism, layer normalization is applied. Also, residual connections are used, which means the input of each sub-layer is added to its output. This helps in mitigating the vanishing gradient problem in deep networks.

Each layer of the encoder may also include a position-wise feed-forward neural network, applied to each position separately and identically. This network consists of fully connected layers with activation functions. Multiple such encoder layers are stacked on top of each other. Each layer operates on the output of the preceding layer.

During use, the text input is converted into a set of vectors through the embedding and positional encoding steps. These vectors are then passed through the multi-head self-attention mechanism, where the model learns to focus on different parts of the input sequence. The output of the attention mechanism is then normalized and passed through the feed-forward neural network. The process is repeated for each encoder layer, with the output of one layer feeding into the next. The final output of the Transformer encoder is a set of vectors, one for each input token.

The goals also may be selected from a drop down entry or other selection choices. The system then has a search algorithm that uses the processed query to search through a database of videos. The video database is illustrated as block 404 in FIG. 4 and block 504 in FIG. 5.

This database may be internally maintained or the algorithm may interface with online video platforms like YouTube or Vimeo through their APIs. The search algorithm retrieves a list of videos that match the query and recommends one or more videos of which the user will be inserted into. The videos are stored with a title, a brief description, and a thumbnail image for each video whereby the video is then sent to the image generation system for video or image generation to have the target user replace the entities in that video. The Adaptive Content Curator Engine is illustrated as block 405 in FIG. 4 and block 505 in FIG. 5.

Adaptive Content Curator Engine 405 may be a specialized recommendation engine within the entire framework that utilizes data processed by the Health Data Processing system (410). The Adaptive Content Curator Engine is an artificial intelligence system that creates personalized and positive motivational stories for patients related to the targeted disease, drawing insights from the individual's health monitoring parameters. It is designed to continually enhance its understanding and decision-making capabilities in the realm of content creation by processing and analyzing feedback derived from a diverse set of health monitoring parameters thus refining its content and recommendations over time. This system employs advanced algorithms to learn patterns, identify correlations, and adapt its recommendations or interventions over time, aiming to optimize and personalize the content curated for individuals. Based on all the inputs this engine first generates a story/narrative and then a video is automatically curated based on that storyline.

The system may include a feedback mechanism where users may indicate whether the videos were relevant or not similar to the other feedback mechanism introduced later. This feedback may be used to further train and refine the search algorithm.

Concurrently or subsequently, visualization system 100 may perform many tasks once content has been received by user 120 whereby the system may use a deepfake system to implement the content from the user into another image or video to create a curated output image having the user in a scenario where they are achieving their goal or overcoming their ailment. The deepfake video generator is illustrated as block 406 in FIG. 4 and block 506 in FIG. 5.

As discussed, visualization system 100 may analyze the image or video collection module for categorizing and to determine which image should be utilized when creating a deepfake image or video. It may analyze multiple objects if the user wishes to insert multiple people into this scenario such as a significant other. To accomplish this, the content processing module may begin image processing on the content received.

The Adaptive Content Curator Engine is designed to identify people's faces that could be utilized in the deepfake generation. For persons, the content processing module generates correlation information that is an identity, or more generally, identification information to the person. This information may consist of race, ethnicity, gender classification, hair color, shape or any other features necessary. For facial recognition, the content processing module may in addition or instead use data from one or more databases 450, social networking sites, professional data services, or other such entities. It will use these characteristics of the user for personalized content creation ensuring the recommended video seems relatable.

For the purposes of background/context generation this module may also be trained for analysis of objects or environment, for example: geography of the user. Processes may be performed by the content processing module on objects which enable classifications to be associated with the objects into a hierarchical structure to facilitate analysis, searching, and recognition of identifiers.

Figure 6:
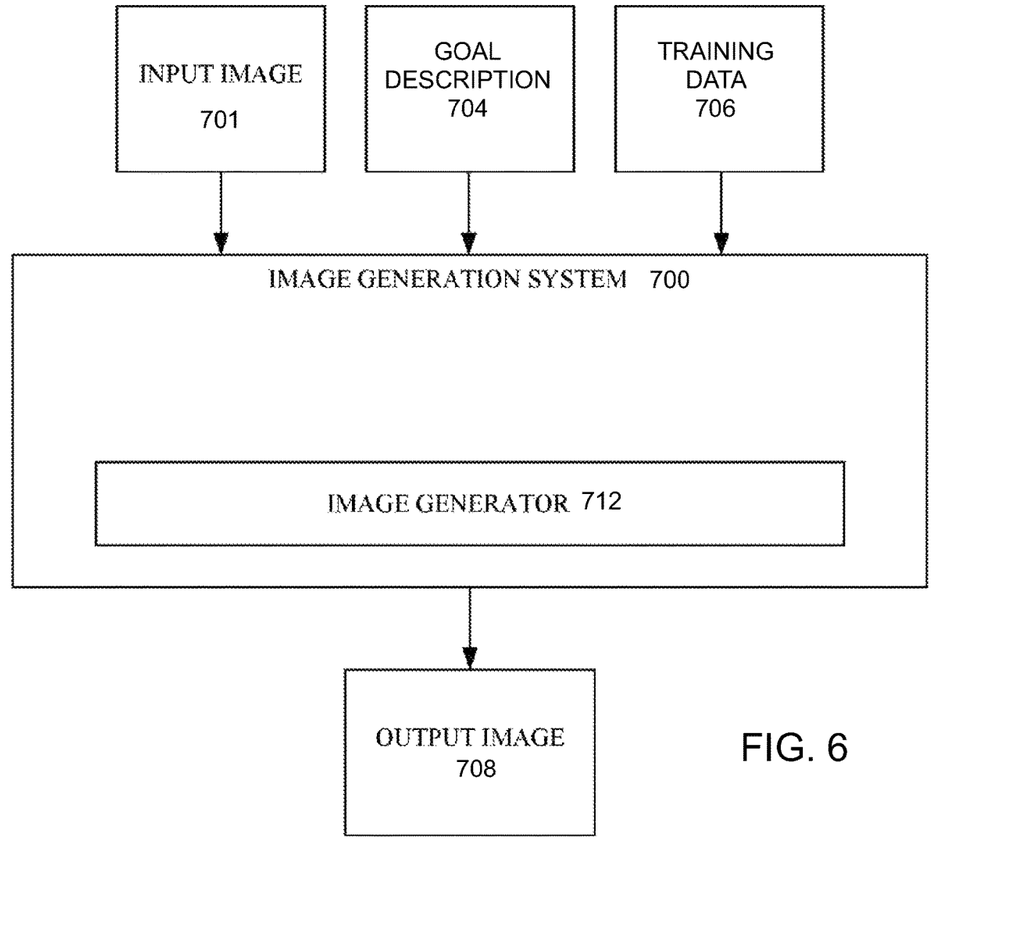
FIG. 6 illustrates the image generation training system.
Figure 7:
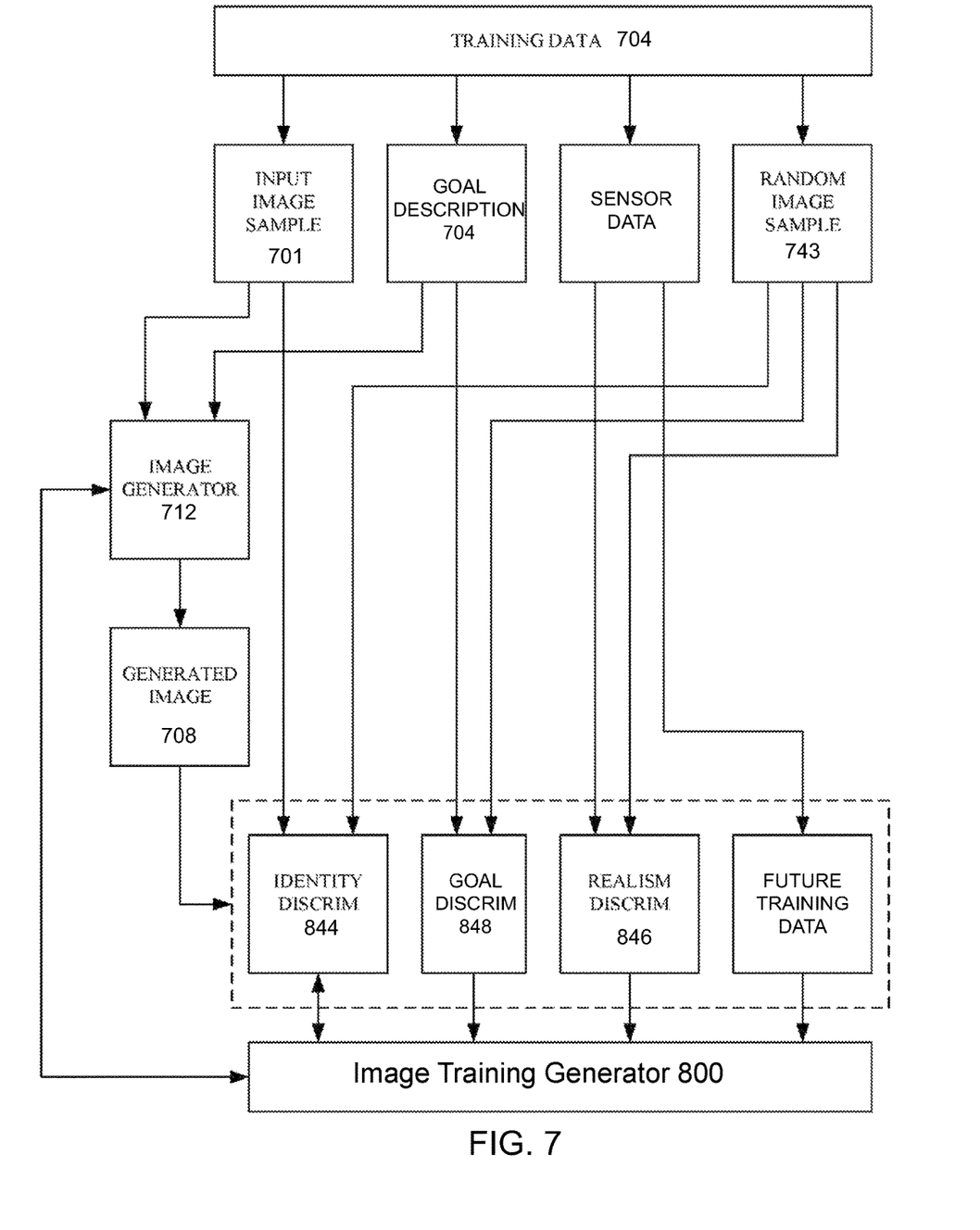
FIG. 7 illustrates the flow operation of the image generation training system.

Visualization system 100 employs specialized deepfake technology, utilizing image generation systems including an image generator 712 and image generation training system 800. These systems generate images or videos based on a reference image, allowing for the integration of user 120's input image into simulated scenarios or events. During inference, a single reference image can produce an image resembling the subject of the reference image but featuring the user in a new context. This simulated image is not a real photograph but a representation of the subject's appearance applied to the rendered target image, achieved by mapping facial features from the reference image onto the target image.

Visualization system 100 employs specialized deepfake technology, utilizing image generation systems including an image generator 712 and image generation training system 800. These systems generate images or videos based on a reference image, allowing for the integration of user 120's input image into simulated scenarios or events. During inference, a single reference image can produce an image resembling the subject of the reference image but featuring the user in a new context. This simulated image is not a real photograph but a representation of the subject's appearance applied to the rendered target image, achieved by mapping facial features from the reference image onto the target image.

Visualization system 100 is trained to constrain generation of the output image based on the input image such that the output image appears to depict the subject of the input image. The image generator may be part of a generative adversarial network that is trained by concurrently training the generator to generate images and concurrently training a discriminator to determine whether images are real or not real, correspond to the image from the rendered version of the image, and correspond to the identity of the subject from the reference image.

As discussed, image generation system 700 receives content such as an input image 701 (which may also be called a reference image) and a goal or ailment description received from user 120. The image generation system 700 generates an output image 708 that may be displayed as an illustration of a possible goal to achieve for user 120 or an ailment to overcome. It should be appreciated that image may be used interchangeably with video whereby the system may generate both from an image. The image generation system 700 is configured to generate the output image such that it appears to depict the person who is depicted in the input image 701 but with modifications made relative to the input image 701 in accordance with the goal or ailment description.

The input image 701 may be a still image that shows a person. The person who is depicted in the input image 701 may be referred to herein as the subject of the input image 701. As an example, the input image 701 may be a headshot image that shows the person's face. The input image 701 may be a digital image composed of pixels arranged in a grid. The input image 701 may be encoded in any suitable format and color space that allow interpretation of the input image 701 by the image generation system 700. In some implementations, one or more still image frames are used as the input image 701. In some implementations, one or more video frames are used as the input image 701.

The goal or ailment description 704 is an input to the image generation system 700 that describes a target situation or event to be shown in the output image 708 along with previous training data 706 that will be discussed later. The goal or ailment description 704 is an encoded (i.e., using numerical values) representation of a goal. The goal or ailment description 704 may include a value or combination of values that represent commonly understood goals that correspond to any number of events such as a promotion, graduation, finding love, as well as overcoming an ailment or health related concern such as cancer.

The output image 708 may be a still image that shows a synthetic image of a person who appears to be the subject of the input image 701. The output image 708 is generated based on the input image 701 and such that the subject of the input image is depicted in accordance with the goal or ailment description 704. The output image 708 may be a digital image composed of pixels arranged in a grid. The output image 708 may be encoded in any suitable format and color space. In some implementations, multiple still images or video frames are generated as outputs by the image generation system 700.

The image generation system 700 operates as a machine learning-based platform, utilizing input images 701 and goal or ailment descriptions 704 to produce the output image 708. This system employs neural networks, interconnected units that process inputs and generate outputs based on activation functions. For instance, neurons within the network can detect specific features within an image and respond accordingly.

Similarly, the system analyzes audio samples from users 120, employing voice recognition and generation algorithms to replicate voices. By assessing parameters like pitch, tone, and tempo, the AI extracts unique vocal characteristics, which are then utilized by an audio generator training system akin to the image generation system. With further training and refinement, the synthesized voice quality improves, capturing the nuances of users 120's voices more accurately.

During training, the network's behavior is established through iterations, adjusting connection strengths (weights) between neurons based on discrepancies between output and expected results (ground truth). Through repeated iterations, the network converges to produce outputs consistent with the ground truth. Once training is complete, the network's weights remain constant, ensuring consistent performance.

FIG. 6 illustrates the image generation training system 800, designed to train the image generation system 700 in generating synthetic images aligned with learned constraints. This system adopts a generative adversarial network (GAN) framework, where a generator produces synthetic images, a discriminator distinguishes real from synthetic images, and both are iteratively trained based on their performance.

The image generation training system 800 utilizes training data 706 and employs a machine learning model, like a neural network, within the image generation system 700. This system aims to produce an output image 708 that aligns with the user's goal or ailment while resembling the input image 701.

The discriminators within the image generation training system 800 include an identity-based discriminator 844, a realism-based discriminator 846, and a scene adjustment discriminator 848. The identity-based discriminator 844 assesses whether the subject in the generated image 708 matches the one in the input image 701. It distinguishes correct results when depicting the same person and evaluates the realism-based discriminator 846 to distinguish real from synthetic images.

The realism-based discriminator 846 evaluates the authenticity of the generated image 708, determining whether it resembles a real or synthetic image. Correct classification as a real image is desired for the generator's performance. Both discriminators are trained iteratively with feedback from the training process to refine the image generation system 700.

In the described approach, the realism-based discriminator can be realized as a GAN discriminator, providing realism evaluations on a per-image basis. Alternatively, a Patch GAN discriminator can be employed, dividing the image into overlapping patches and assessing realism at the patch level. This approach enables fine-grained determinations of correctness or incorrectness for training the image generation system 700.

During use, once the deepfake has been created and has reached an adequate result such that the outputted image will appear realistic, users 120 can visualize themselves achieving goals or overcoming ailments by viewing the outputted image or video. This visualization occurs via display 270 on computing device 112 through API 286, facilitating user engagement and motivation. This is illustrated as block 407 and 408 in FIG. 4 and block 507 and 508 in FIG. 5.

While visualizing the goal, visualization system 100 may then receive biofeedback from a health data processing system that may be connected to a user while at the hospital or other location during the viewing of the image or video to monitor how user 120 is reacting to the video as well as gauge any possible adjustments needed in real time or future alignment with their ailments or from inadequate results.

Health data processing system is a comprehensive system designed to collect, aggregate, and process diverse health monitoring parameters from various sources. This platform employs advanced data processing techniques to clean, normalize, and integrate health data, ensuring a cohesive and standardized dataset. The processed data is then fed into an AI system, such as the Adaptive Content Curator Engine, to facilitate continuous learning, pattern recognition, and improvement over time. By integrating data from vital signs, laboratory tests, and other health metrics, the Health Data Processing system strives to provide more accurate, timely, and individualized insights, ultimately contributing to the improvement of the content created by the Adaptive Content Curator Engine thereafter. It hence plays a crucial role in enhancing the accuracy and efficacy of our AI-driven health optimization processes. This is illustrated as block 409 in FIG. 4. They may also provide manual feedback in the form of responses as illustrated in block 509 of FIG. 5.

To accomplish this, Visualization System 100 employs one or more trained machine learning algorithms, such as a neural network within the health data processing system, to adapt videos based on various health monitoring parameters, as depicted in block 410 of FIG. 4. A neural network mimics the human cognitive system and comprises layers of neurons or nodes, including an input layer for data presentation, internal layers, and an output layer. The complexity of the problem dictates the number of neurons in each layer.

A convolutional neural network (CNN), deep neural network (DNN), or recurrent neural network (RNN) may process previous various health monitoring parameters, output images and videos, and user responses. These inputs are received by the input layer, where the interface layer clusters them to present ailments inputted by user 120. The output layer then adjusts the output images and videos based on variables like user reactions or the inadequacy of the input image.

An overall score reflecting the user's positive reaction for each video may be determined and stored in the databases. Real-time data recording and processing by the Adaptive Content Curator engine correlate a patient's health data parameters with different scenes or moments in the outputted video, aiding in improvement over time through reinforcement learning.

Additionally, the system analyzes audio samples of users 120, extracting features characteristic of their voice such as pitch, tone, and tempo. These features can be used as verbal feedback for the output video or to personalize content delivery. The extracted features are fed into an audio generator training system similar to the image generator system, with further refinement possible through additional data or model fine-tuning.

The system interprets the goals and then generates a video or image using the likeness of the user. After successfully receiving questionnaires and scores overtime, visualization system 100 may retrieve data associated with users 120 whereby the system may apply this data to future assessments of other users with similar biographic information or input data who may be trying to achieve various goals or overcome various ailments such that successful results of previous users may assist future users. Depending on the situation, this information may also be relayed or notified to third-party systems depending on the score or how many times the score has been reached over a predetermined time period.

In other non-limiting embodiments, the technologies used to create videos are instead applied to create a story describing a user fulfilling their goals. In this embodiment, the user provides an input regarding their goal, which could be a prompt, a few keywords, or even a sentence. The system interprets this input to understand the context and the intent behind it. Based on the input and what the model has learned during its training, it generates text that forms a story. This involves creating characters, settings, plot points, and other narrative elements that are woven into a coherent narrative for the user fulfilling their goal. Some systems may include an additional step where the generated story is refined. This could involve grammar checks, style adjustments, user background considerations or making sure the story remains relevant, consistent and coherent from start to finish. The system presents the generated story to the user. The user may then read the story, provide feedback, or use the story whereby they may enter information through the user interface to guide the path of the story to next levels similar to a choose your own adventure book. Similar to the deep fake video described above, the system could also present the user with a relevant deep fake image related to the user fulfilling the goal as will be depicted in the story.

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description but is not intended to be exhaustive or limited to the invention in the form disclosed. Many modifications and variations will be apparent to those of ordinary skill in the art without departing from the scope and spirit of the invention.

What is claimed:

1. A system for personalized storyline generation comprising:
wherein the system is configured for:
receiving input from one or more user computing device systems of a user describing their desired goal;
interpreting the desired goal from the input that is received from the one or more user computing device systems associated with the user;
producing visualization content in response to the desired goal depicting a generated format with the user experiencing the desired visualization goal utilizing a deepfake module to curate realistic and personalized visual content of the user themselves experiencing the desired goal;
presenting the visualization content on the one or more user computing device systems for the user to experience personalized video storylines addressing a specific life situation;
analyze accumulated user data from a plurality of users to identify patterns and form user clusters with shared characteristics; and
enhance content personalization for the user based on identified patterns and the user clusters, wherein the system employs a standardized health index to normalize diverse health metrics into a unified scale and trigger dynamic content adjustments using methodology of reinforcement learning when the index falls outside a predefined threshold range.

2. The system of claim 1 wherein the specific life situation is overcoming a medical condition, wherein the system is further configured to: processing diverse health monitoring parameters from various sources that incorporates real-time health data processing to inform and influence the visualization content, wherein utilization of the diverse health monitoring parameters is recorded from the user either during or after application to tailor the visualization content to user's health and well-being; and
create positive motivational stories for the user related to a targeted disease in response to the diverse health monitoring parameters of the user.

3. The system of claim 2 wherein the system is further configured to:
connecting to one or more hospital systems; and
accessing patient files.

4. The system of claim 1, wherein the visualization content is in a form of a generated video, image, or story, illustrating the user as accomplishing a goal or overcoming an ailment.

5. The system of claim 1, wherein the visualization content is designed for the user to overcome medical challenges, fostering a positive mindset, and supporting a recovery process and to depict the user successfully navigating and overcoming health-related obstacles.

6. The system of claim 3, further comprising a security module to ensure compliance with healthcare privacy regulations in processing and storing user health data.

7. The system of claim 6, wherein the visualization content also assists the user to overcome obstacles in life including addressing financial challenges by creating personalized video narratives depicting users successfully overcoming debt or financial obstacles.

8. The system of claim 2, wherein the one or more user computing device systems are virtual reality glasses or augmented reality glasses wherein the visualization content is produced on screens of the virtual reality glasses or the augmented reality glasses, wherein a voice of the user is implemented into the visualization content, wherein overlay annotations, comments, or virtual objects are positioned onto an environment.

9. The system of claim 1, wherein the system is further configured to:
incorporating additional individuals into the visualization content using deepfake technology to represent real-life relationships of the user.

10. A method of personalized storyline generation using an adaptive content curator engine depicts a user overcoming challenges, achieving goals, or addressing specific life situations, the method comprising:
utilizing a search algorithm to process queries by the user;
searching an internally maintained video database for a video; and
creating a deepfake of the user themselves in the video to create realistic and personalized visual content, wherein the method is used to assist the users in overcoming medical challenges, fostering a positive mindset, or supporting a recovery process.

11. The method of claim 10, further comprising processing diverse health monitoring parameters and user feedback with one or more wearables to dynamically refine understanding and recommendations over time, and employing a standardized health wherein index diverse health metrics are normalized into a unified scale and dynamic content adjustments are trigged when the index falls outside a predefined threshold range.

12. The method of claim 11, further comprising utilizing an immersive experience wherein personalized video content is provided in a virtual or augmented environment to enhance user immersion and create a more engaging and realistic user experience in visualizing their desired outcomes, wherein overlay annotations, comments, or virtual objects are positioned onto an environment.

13. A system for personalized visualization content generation comprising:
a content processing module configured to collect and analyze user-provided images;
a deepfake video generator configured to create personalized visualization content depicting a user achieving specified goals for the user;
a health data processing system configured to collect and process health monitoring parameters during content viewing; an adaptive content curator engine configured to refine the visualization content based on the processed health monitoring parameters; and
a display configured to present the visualization content through virtual reality or augmented reality devices.

14. A method for generating personalized visualization content comprising:
receiving user profile information and user face images;
receiving a desired goal from user;
analyzing the user profile information including user demographics, current state, user interaction data, and the desired goal to create a personalized storyline, which is then supplied as an input to a video generation system to create a personalized video using generative artificial intelligence technology; and
adding additional level of personalization to the generated video by using a deepfake mechanism
using deepfake technology, the personalized visualization content depicting the user themselves achieving the desired goal; monitoring health parameters during content viewing;

processing the health parameters to generate feedback; and refining future content generation based on the processed feedback.

15. A system for therapeutic visualization comprising:
a video generation system configured to: receive input images of a user; receive goal descriptions; generate output videos using generative adversarial networks;
a health data processing system configured to: collect health monitoring parameters; process the health monitoring parameters; provide feedback for content refinement; and
an adaptive content curator engine configured to: generate personalized content based on the processed health parameters; refine content based on user feedback and the health monitoring parameters.

16. A method for generating personalized therapeutic content comprising: processing a user query through a narrative generation system to create personalized story scripts; incorporating therapeutic elements designed to foster positivity and mindset transformation; adapting story elements based on a user's current situation and recovery progress; creating personalized videos using generative artificial intelligence technologies selected from the group consisting of Generative Adversarial Networks (GANs) and diffusion models for video synthesis; and
presenting the personalized videos to the user through a display device.

* * * * *